(12) United States Patent
Wilmet et al.

(10) Patent No.: US 6,841,706 B1
(45) Date of Patent: Jan. 11, 2005

(54) HYDROFLUORINATION CATALYST AND METHOD

(75) Inventors: Vincent Wilmet, Wavre (BE); Georges Lejeune, Dolhain-Limbourg (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 09/807,285

(22) PCT Filed: Oct. 11, 1999

(86) PCT No.: PCT/EP99/07782

§ 371 (c)(1),
(2), (4) Date: Jun. 19, 2001

(87) PCT Pub. No.: WO00/21660

PCT Pub. Date: Apr. 20, 2000

(30) Foreign Application Priority Data

Oct. 12, 1998 (BE) .............................. 9800732

(51) Int. Cl.$^7$ .................. C07C 17/00; C07C 17/08; C07C 19/08; B01J 27/24; B01J 23/00
(52) U.S. Cl. ............... 570/169; 570/165; 570/166; 570/168; 570/167; 502/319; 502/200
(58) Field of Search ................... 570/169, 165, 570/166, 168, 167; 502/200, 319

(56) References Cited

U.S. PATENT DOCUMENTS

| 5,475,167 A | 12/1995 | Nappa et al. ................ 570/169 |
| 5,600,039 A | 2/1997 | Galland et al. .............. 570/169 |
| 5,672,786 A * | 9/1997 | Bonniface et al. .......... 570/165 |

FOREIGN PATENT DOCUMENTS

| AU | 80339 | 9/1997 |
| AU | 682225 | 9/1997 |
| CA | 861572 | 1/1971 |
| EP | 554 165 | 8/1993 |
| EP | 657 409 | 12/1994 |
| EP | 657 409 | 6/1995 |
| EP | 776 878 | 6/1997 |
| WO | 92/19576 | 11/1992 |

* cited by examiner

*Primary Examiner*—Elvis O. Price
(74) *Attorney, Agent, or Firm*—Connolly Bove Lodge & Hutz LLP

(57) ABSTRACT

Hydrofluorination catalyst based on a chromium oxide which is poor in ammonium salts.

20 Claims, No Drawings

HYDROFLUORINATION CATALYST AND METHOD

The present invention relates to a hydrofluorination catalyst based on chromium oxide used in particular to convert halogenated hydrocarbons under the action of hydrogen fluoride.

A great many catalysts have been described for the hydrofluorination reaction of halogenated aliphatic hydrocarbons under the action of hydrogen fluoride. Mention has generally been made of oxides or halides of chromium, aluminium, titanium, nickel, tin, antimony or other metals, used as such or deposited on a support, such as active charcoal, graphite or alumina.

The widely used chromium catalysts include mainly chromium fluorides, chromium oxyfluorides and chromium oxides, mainly chromium sesquioxide ($Cr_2O_3$).

Canadian Patent CA 861 572 discloses the synthesis and use of anhydrous chromium oxide as catalyst in hydrofluorination reactions of chlorinated or brominated hydrocarbons. However, no information is given with regard to the purity of the catalyst obtained according to the preparation processes disclosed in the patent.

Patent Application WO 92/19576 discloses the use of chromium oxide as hydrofluorination catalyst in the presence of hydrogen fluoride and its preparation by thermal decomposition of ammonium dichromate. The presence of traces of alkali metals and more particularly of potassium is very harmful to the activity of this catalyst.

It transpires that the activity of chromium oxide as hydrofluorination catalyst can vary in particular as a function of its preparation process, of its specific surface area, of its state of crystallinity, of the oxidation state of the chromium or of its amorphous nature without, however, a coherent explanation with regard to its activity being provided.

The Applicant Company has found that the catalytic activity of a catalyst based on chromium oxide is highly dependent on the amount of ammonium salts present in the catalyst. More particularly, the Applicant Company has found that the catalytic activity of such a catalyst is inversely proportional to the amount of ammonium salts present as impurity in the catalyst.

One object of the present invention is consequently to provide a hydrofluorination catalyst based on chromium oxide which is poor in ammonium salts.

The ammonium salts present in the catalyst can exist in particular in the form of an ammonium halide, such as ammonium chloride or ammonium fluoride, or in the form of another inorganic or organic acid salt, such as ammonium nitrate, ammonium chromate, ammonium bichromate or ammonium acetate.

The catalysts according to the invention typically include less than it of ammonium salts. They preferably exhibit a content of ammonium salts of less than or equal to 0.5% by weight. The content of ammonium ions in the catalyst is preferably less than or equal to 0.2% by weight. Excellent results are obtained with a catalyst for which the content of ammonium ions is less than or equal to 0.1% by weight. Particularly advantageous results are obtained with a catalyst for which the content of ammonium ions is less than or equal to 0.05% by weight.

By convention, in the present description, the values mentioned for the content of ammonium salts in the catalyst according to the invention relate to the content of $NH_4^+$ ions with respect to the content of chromium in the catalyst, expressed in the form of $Cr_2O_3$.

The chromium oxide used in the catalyst according to the present invention can exhibit a variable specific surface area greater than or equal to 20 $m^2/g$ and less than or equal to 500 $m^2/g$, determined according to the BET (Brunauer Emmet Teller) method. Generally, the pore volume of the catalyst, determined according to the nitrogen adsorption method, is greater than or equal to 0.05 $cm^3/g$ and less than or equal to 1 $cm^3/g$. The catalyst can be entirely amorphous or entirely crystalline, just as it can be partially amorphous and partially crystalline. The chromium oxide in the catalyst according to the invention is generally essentially in the III oxidation state but the catalyst can also comprise variable amounts of chromium in an oxidation state of greater than III, such as, for example, chromium(VI).

Typically, it can be synthesized according to one of the processes known to a person skilled in the art and more particularly either by reduction of chromium(VI) oxide ($CrO_3$) by an alcohol, such as ethanol, or by dehydration at high temperature of a chromium(III) hydroxide gel or by pyrolysis of ammonium dichromate. In the latter case, the chromium oxide obtained during the high-temperature (generally greater than 500° C.) pyrolysis stage is generally cooled under a stream of air and washed several times until there are no more signs of ammonium ions in the washing solution.

In the catalyst according to the present invention, the chromium oxide can be used either as such, in the bulk form, or it can be deposited on a support, such as active charcoal, graphite, alumina, fluorinated alumina, magnesium oxide, and the like. The catalyst according to the invention is preferably composed of chromium oxide in the bulk form.

It can additionally comprise other metals or salts of other metals and their mixtures as cocatalysts. Mention may be made, among metals or metal salts which can generally be used, of, for example, cobalt, titanium, manganese, tin, antimony, nickel or zinc and their salts and their oxides. The metal derivatives can be incorporated in the chromium catalyst according to various processes, such as impregnation of the chromium oxide by a metal compound, by coprecipitation of precursors or by mixing and milling solid metal compounds.

It is generally advantageous to calcine the catalyst before use. Conventionally, this calcination is carried out under a stream of inert gas at a temperature greater than or equal to 200° C. and less than or equal to 600° C. Advantageously, the calcination temperature is greater than or equal to 250° C. and less than or equal to 450° C. The inert gas is generally chosen from nitrogen or rare gases, such as helium, argon or neon. For economic reasons, nitrogen is preferred. The calcination time is usually between 2 hours and 20 hours. The calcination time is advantageously greater than or equal to 4 hours and less than or equal to 16 hours. The calcination time is preferably greater than or equal to 6 hours and less than or equal to 14 hours.

The catalyst is generally pretreated with hydrogen fluoride before being employed in a hydrofluorination reaction. It is believed that this pretreatment converts the chromium oxide which is found at the surface to chromium oxyfluoride. This pretreatment is generally carried out in a reactor, usually that which is used for the hydrofluorination reactions according to the invention, by passing hydrogen fluoride over the calcined and dried chromium oxide, so as to saturate the chromium oxide with hydrogen fluoride. This pretreatment usually takes place over a period of time ranging from 15 to 300 minutes at a temperature generally of between 200 and 700° C. This pretreatment is often useful but is not essential for the satisfactory operation of the process according to the present invention.

Whatever the method of preparation of the chromium oxide, it is particularly advantageous for the pretreatment with hydrogen fluoride to be carried out on a catalyst based on chromium oxide which is poor or which has been depleted beforehand in ammonium salts.

Another subject-matter of the present invention is a method for the preparation of a catalyst based on chromium oxide which is poor in ammonium salts, typically either by calcination of an appropriate chromium compound at a temperature of 300 to 500° C., preferably while flushing with an inert gas, such as nitrogen, or by washing the crude chromium oxide with water, optionally followed by a stage of processing the chromium oxide with other constituents of the catalyst, by calcination and by treatment with hydrogen fluoride.

Another object of the present invention is to provide a process for the hydrofluorination of halogenated hydrocarbons by the action of hydrogen fluoride on a halogenated hydrocarbon in the presence of such a catalyst.

The term "hydrofluorination" is understood to mean the addition reaction of hydrogen fluoride to a carbon—carbon double bond and the substitution reaction of a halogen atom, generally chlorine or bromine, by a fluorine atom on a saturated substrate.

In the context of the present invention, the hydrofluorination reactions take place under the catalytic action of the catalyst based on chromium oxide, introduced as such into the reaction mixture or fluorinated beforehand by reaction with hydrogen fluoride.

The halogenated hydrocarbon used in the process according to the invention can be an aliphatic alkane corresponding to the general formula $C_wH_xX_yF_z$ (I), in which w is an integer between 1 and 6, x is an integer between 0 and (2w+1), y is an integer between 1 and (2w+1), z is an integer between 0 and (2w+1), the sum (x+y+z) has the value (2w+2) and X represents chlorine or bromine. Advantageously, the halogenated hydrocarbon used in the process according to the invention is an aliphatic alkane corresponding to the formula (I) in which w is an integer between 1 and 4 and x is an integer between 1 and 2w.

Mention may be made, as non-limiting examples of halogenated alkanes used in the process according to the invention, of dichloromethane, chlorofluoromethane, chlorodifluoromethane, 1-chloro-1-fluoroethane, 1,1-dichloro-1-fluoroethane, 1-chloro-1,1-difluoroethane, chlorotetrafluoroethane isomers, dichlorotrifluoroethane isomers, trichlorodifluoroethane isomers, tetrachlorofluoroethane isomers, pentachloroethane or compounds of general formulae $C_3H_3Cl_{(5-z)}F_z$ and $C_4H_5Cl_{(8-z)}F_z$ with z representing an integer which can take the values from 1 to 4.

The halogenated hydrocarbon used in the process according to the invention can also be an aliphatic alkene corresponding to the general formula $C_wH_xX_yF_z$, (I), in which w is an integer between 1 and 6, x is an integer between 0 and (2w−1), y is an integer between 1 and (2w−1), z is an integer between 0 and (2w−1), the sum (x+y+z) has the value 2w and X represents chlorine or bromine. The halogenated hydrocarbon used in the process according to the invention can also advantageously be an aliphatic alkene corresponding to the formula (I) in which w is an integer between 1 and 4.

Mention may be made, as non-limiting examples of halogenated alkenes used in the process according to the invention, of 1,1-dichloroethylene, trichloroethylene, perchloroethylene, vinyl chloride, 3,3,3-trichloroprop-1-ene, 1,1,3-trichloroprop-1-ene, 1,1,3,3-tetrachlorobut-1-ene, 1,1,1,3-tetrachlorobut-2-ene, 1,1,1,3-tetrachlorobut-3-ene, 1,1,4,4,4-pentachlorobut-1-ene, 1,1,1,3-tetrachloroprop-2-ene, 1,1,3,3-tetrachloroprop-1-ene, 1,1,3,3-tetrachloro-2-methylprop-2-ene, 1,1,1,3-tetrachloro-2-methylprop-2-ene, 1,1,1,3,3-pentachloroprop-2-ene, 3-chloro-1,1,1-trifluoroprop-2-ene and the mixtures of these compounds.

An aim of the invention is thus to produce, starting from saturated or unsaturated halogenated hydrocarbons, fluorinated or chlorofluorinated alkanes which comprise more fluorine atoms and fewer chlorine atoms than the reactants used. The invention is targeted in particular at the synthesis of fluorinated hydrocarbons, such as in particular difluoromethane, pentafluoroethane, 1,1,1,2-tetrafluoroethane, 1,1,1-trifluoroethane, 1,1-difluoroethane, 2,2-dichloro-1,1,1-trifluoroethane, 1,1,1-trifluoro-2-chloroethane, 1,1,1,3,3-pentafluoropropane, 1,1,1,3,3-pentafluorobutane, 1,1,1,3,3,3-hexafluorobutane, 1,1,1,3,3-pentafluoro-2-methylpropane and 1,1,1,3,3,3-hexafluoropropane.

A more particular aim of the invention is the preparation of fluorinated alkanes not comprising a chlorine atom under the catalytic action of a chromium oxide which is poor in ammonium salts.

A more particular aim of the invention is to produce, under the action of the catalyst according to the invention, pentafluoroethane by hydrofluorination of perchloroethylene, difluoromethane by hydrofluorination of dichloromethane, 1,1,1,2-tetrafluoroethane by hydrofluorination of 2-chloro-1,1,1-trifluoroethane and 2-chloro-1,1,1-trifluoroethane by hydrofluorination of trichloroethylene.

The hydrofluorination reaction can be carried out in the gas phase or in the condensed phase. The gas phase is preferred.

The process according to the present invention is generally carried out continuously.

The molar ratio of the hydrogen fluoride to the halogenated hydrocarbon employed is usually greater than or equal to 1 and less than or equal to 100. This molar ratio is advantageously greater than or equal to 3 and less than or equal to 50. This molar ratio is preferably greater than or equal to 4 and less than or equal to 20.

The reaction pressure is not critical. A pressure of between 1 and 10 bar is usually highly suitable.

The reaction temperature is generally between ambient temperature and 600° C. The reaction temperature is advantageously greater than or equal to 100° C. and less than or equal to 500° C. The reaction temperature is preferably greater than or equal to 200° C. and less than or equal to 450° C.

Generally, the higher the reaction temperature, the greater the HF/halogenated hydrocarbon molar ratio and the longer the contact time, the higher the degree of conversion of the reactants to fluorinated hydrocarbons and the greater the degree of hydrofluorination. The parameters mentioned above can be adjusted so as to obtain the desired product with high selectivity, a high degree of conversion and a high yield.

The unconverted reactants and the intermediate compounds can advantageously be recycled in the hydrofluorination reactor to increase the productivity with respect to the desired fluorinated product.

The process according to the invention can be carried out in any type of reactor or apparatus which is resistant to pressure, to hydrogen fluoride and to hydrogen chloride and, in the case of a continuous process, which makes it possible to continually maintain a substantially stable composition of the reaction mixture. The process according to the invention is generally carried out continuously in a gas phase reactor equipped with a device for introducing the reactants, in the liquid or gas phase, and for withdrawing a gas stream, for example in a tubular reactor filled with a stationary catalyst bed.

The optimum residence time, expressed as the ratio of the total throughput of the reactants (at reaction temperature and pressure) to the free volume of the reactor, can generally vary from 5 seconds to 10 minutes.

The examples below illustrate the invention without implied limitation. In these examples, the degree of conversion of the halogenated hydrocarbon is the ratio of the amount employed, decreased by the amount unconverted, to the amount employed, multiplied by 100; the selectivity for fluorinated or chlorofluorinated alkane is the ratio of the amount of fluorinated or chlorofluorinated alkane formed to the amount which would have been formed if all the halogenated hydrocarbon converted had generated fluorinated or chlorofluorinated alkane; the overall selectivity is the sum of the selectivities of all the intermediates which can be recovered as the desired fluorinated or chlorofluorinated alkane; the yield of fluorinated or chlorofluorinated alkane is the product of the degree of conversion by the selectivity for this fluorinated or chlorofluorinated alkane.

EXAMPLES 1-10

20 cm$^3$ of bulk chromium oxide including a variable content of NH$_4^+$ and a hydrogen fluoride/perchloroethylene (PER) mixture in a molar ratio of 10 mol/mol were introduced into a cylindrical autoclave with an internal diameter of 15 mm. The reaction pressure was maintained at 1 bar and the temperature at 350° C. The residence time was 12.5 seconds. The main product obtained is 1,1,1,2,2-pentafluoroethane (HFC-125).

The results are collated in Table I below.

TABLE I

| Test No. | [NH$_4^+$] (%) | Degree of conversion of the PER (%) | Yield of HFC-125 (mol %) | Overall selectivity (mol %) |
|---|---|---|---|---|
| 1 | 0.27 | 43 | 12 | 73 |
| 2 | 0.17 | 63 | 30 | 79 |
| 3 | 0.11 | 69 | 34 | 81 |
| 4 | 0.07 | 85 | 47 | 80 |
| 5 | 0.05 | 96 | 58 | 81 |
| 6 | 0.001 | 95 | 58 | 85 |
| 7 | 0.001 | 96 | 59 | 85 |
| 8 | 0.001 | 97 | 60 | 84 |
| 9 (C) | 6.5 | 7 | 0.2 | 85 |

(C) indicates a comparative example, not in accordance with the invention.

What is claimed is:

1. A hydrofluorination catalyst based on chromium oxide which contains ammonium salt and which exhibits a content of ammonium salts of less than or equal to 0.2% by weight, expressed in the form of NH4+, with respect to the content of chromium in the catalyst, expressed in the form of Cr2O3.

2. The catalyst according to claim 1, in which the content of ammonium salts is less than or equal to 0.1% by weight of ammonium salts.

3. The catalyst according to claim 1, additionally comprising other metals or salts of other metals and their mixtures as cocatalyst.

4. A process for the hydrofluorination of a halogenated hydrocarbon which comprises reacting a halogenated hydrocarbon with hydrogen fluoride in the presence of the catalyst according to claim 1.

5. The process according to claim 4, wherein the halogenated hydrocarbon is an aliphatic alkane corresponding to the general formula CwHxXyFz (I), wherein w is an integer between 1 and 6,
x is an integer between 0 and (2w+1),
y is an integer between 1 and (2w+1),
z is an integer between 0 and (2w+1),
the sum (x+y+z) has the value (2w+2) and
X represents chlorine or bromine.

6. The process according to claim 4, wherein the halogenated hydrocarbon is an aliphatic alkene corresponding to the general formula CwHxXyFz (I), wherein w is an integer between 1 and 6,
x is an integer between 0 and (2w−1),
y is an integer between 1 and (2w−1),
z is an integer between 0 and (2w−1),
the sum (x+y+z) has the value 2w and
X represents chlorine or bromine.

7. The process according to claim 4, wherein the reaction of the halogenated hydrocarbon with the hydrogen fluoride takes place in a gas phase.

8. The process according to claim 4, wherein difluoromethane is produced by reacting hydrogen fluoride and dichloromethane.

9. The process according to claim 4, wherein 1,1,1,2-tetrafluoroethane is produced by reacting hydrogen fluoride and a compound chosen from trichloroethylene or 2-chloro-1,1,1-trifluoroethane.

10. The process according to claim 4, wherein pentafluoroethane is produced by reacting hydrogen fluoride and a compound selected from the group consisting of perchloroethylene, fluorotetrachlorethane, difluorotrichloroethane, trifluorodichloroethane and chlorotetrafluoroethane.

11. The catalyst as claimed in claim 1, which consists essentially of bulk chromium oxide which contains ammonium salt and which exhibits a content of ammonium salts of less than or equal to 0.2% by weight, expressed in the form of NH4+, with respect to the content of chromium in the catalyst, expressed in the form of Cr2O3.

12. The catalyst according to claim 11, in which the content of ammonium salts is less than or equal to 0.1% by weight of ammonium salts.

13. A process for the hydrofluorination of a halogenated hydrocarbon which comprises reacting a halogenated hydrocarbon with hydrogen fluoride in the presence of the catalyst according to claim 11.

14. The process according to claim 13, wherein the halogenated hydrocarbon is an aliphatic alkane corresponding to the general formula CwHxXyFz (I), wherein w is an integer between 1 and 6,
x is an integer between 0 and (2w+1),
y is an integer between 1 and (2w+1),
z is an integer between 0 and (2w+1),
the sum (x+y+z) has the value (2w+2) and
X represents chlorine or bromine.

15. The process according to claim 13, wherein the halogenated hydrocarbon is an aliphatic alkene corresponding to the general formula CwHxXyFz (1), wherein w is an integer between 1 and 6,
x is an integer between 0 and (2w−1),
y is an integer between 1 and (2w−1),
z is an integer between 0 and (2w−1),
the sum (x+y+z) has the value 2w and
X represents chlorine or bromine.

16. The process according to claim 13, wherein the reaction of the halogenated hydrocarbon with the hydrogen fluoride takes place in a gas phase.

17. The process according to claim 13, wherein difluoromethane is produced by reacting hydrogen fluoride and dichloromethane.

18. The process according to claim 13, wherein 1,1,1,2-tetrafluoroethane is produced by reacting hydrogen fluoride and a compound chosen from trichloroethylene or 2-chloro-1,1,1-tri fluoroethane.

19. The catalyst according to claim 1, wherein content of ammonium salts is less than or equal to 0.05% by weight.

20. The catalyst according to claim 11, wherein content of ammonium salts is less than or equal to 0.05% by weight.

* * * * *